United States Patent
Goldstein et al.

(10) Patent No.: US 7,602,950 B2
(45) Date of Patent: Oct. 13, 2009

(54) MEDICAL SYSTEM ARCHITECTURE FOR INTERACTIVE TRANSFER AND PROGRESSIVE REPRESENTATION OF COMPRESSED IMAGE DATA

(75) Inventors: Markus Goldstein, Würzburg (DE); Norbert Strobel, Palo Alto, CA (US)

(73) Assignee: Siemens Aktiengesellschaft, Munich (DE)

( * ) Notice: Subject to any disclaimer, the term of this patent is extended or adjusted under 35 U.S.C. 154(b) by 745 days.

(21) Appl. No.: 10/788,619

(22) Filed: Feb. 27, 2004

(65) Prior Publication Data
US 2004/0230613 A1    Nov. 18, 2004

(30) Foreign Application Priority Data
Feb. 28, 2003    (DE) ............... 103 09 165

(51) Int. Cl.
*G06K 9/00* (2006.01)
(52) U.S. Cl. ........................ 382/128; 382/232
(58) Field of Classification Search .............. 382/128, 382/232
See application file for complete search history.

(56) References Cited

U.S. PATENT DOCUMENTS 6,795,723 B1 * 9/2004 Liu ............... 600/410
2002/0057844 A1 * 5/2002 Sirohey et al. ............... 382/240
2002/0068863 A1 * 6/2002 Slack ......................... 600/407
2003/0005464 A1 * 1/2003 Gropper et al. ............. 725/115
2003/0018750 A1 * 1/2003 Onno et al. ................. 709/219
2003/0200234 A1 * 10/2003 Koppich et al. ............. 707/203

FOREIGN PATENT DOCUMENTS

WO    WO 00/30012    5/2000

OTHER PUBLICATIONS

"Bildgebende Systeme für die Medizinische Diagnostik," Morneburg (1995) pp. 684-696.

* cited by examiner

*Primary Examiner*—Vikkram Bali
*Assistant Examiner*—Eueng-Nan Yeh
(74) *Attorney, Agent, or Firm*—Schiff Hardin LLP

(57) ABSTRACT

In a medical system architecture and method for interactive transmission and progressive representation of compressed image data of multi-component images, image data are obtained at least one modality with computer workstations being associated with the respective modalities to process the examination images. A device is provided to transfer the examination images; and a device is provided for storage of data and examination images; and further user workstations are provided for post-processing of the examination images. The image data are compressed and organized and stored in packets with specific parameters such that access to individual packets is possible; and the packetized data are decompressed packet-by-packet based on a request from a user workstation, such that multi-component images are generated with progressive parameters.

10 Claims, 4 Drawing Sheets

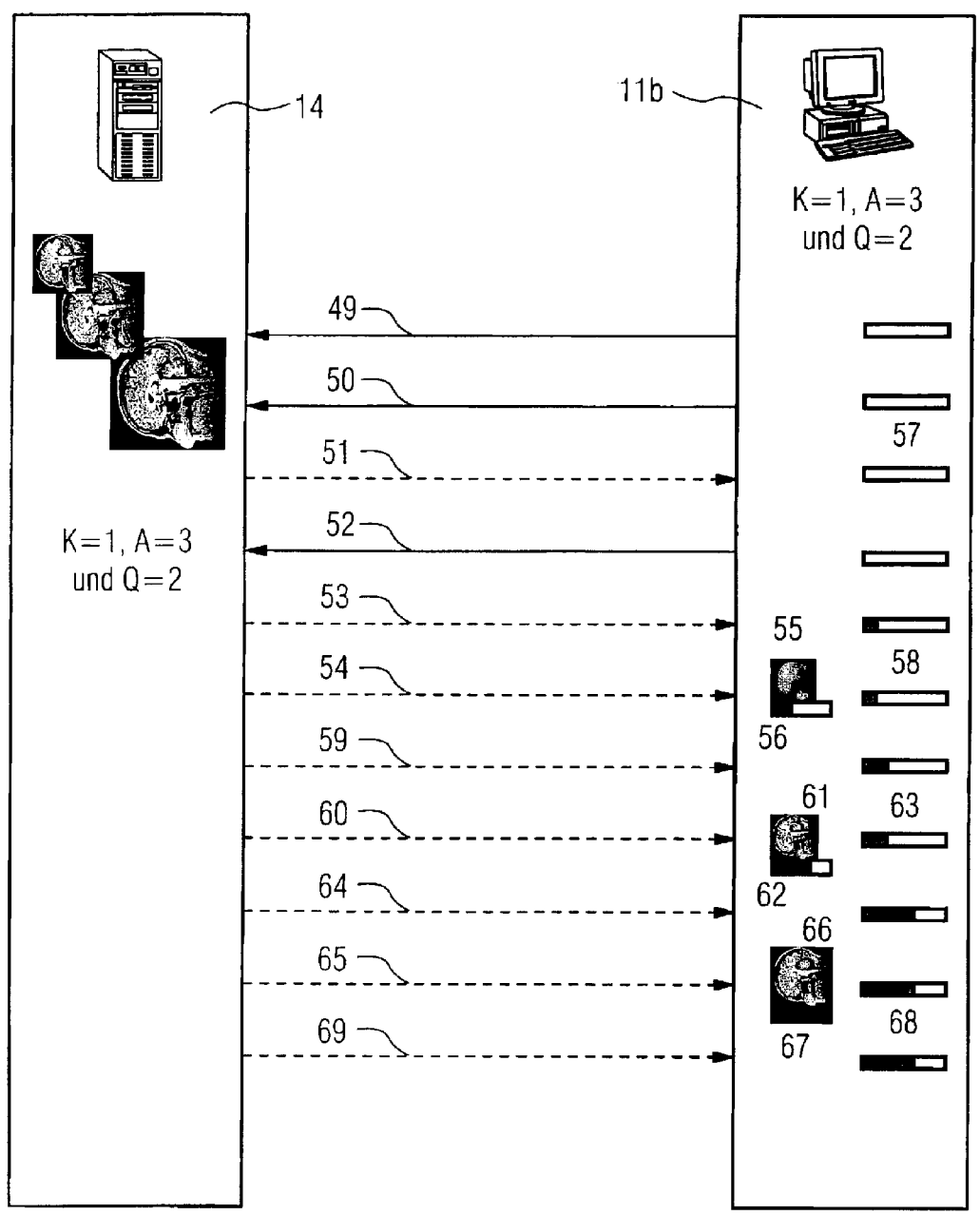

MEDICAL SYSTEM ARCHITECTURE FOR INTERACTIVE TRANSFER AND PROGRESSIVE REPRESENTATION OF COMPRESSED IMAGE DATA

BACKGROUND OF THE INVENTION

1. Field of the Invention

The invention concerns a medical system architecture to transfer and represent image data of medical multi-component images, of the type having at least one modality to acquire examination images; computer workstations associated with the respective modalities to process the examination images; a device to transfer the examination images; a device for storage of data and the examination images; and with further user workstations for post-processing the examination images. The invention also concerns a method to operate such a medical system architecture.

2. Description of the Prior Art

Known from the book "Bildgebende Systeme für die medizinische Diagnostik", published by H. Morneburg, 3rd edition, 1995, pages 684 et seq. are medical system architectures, known as PACS (Picture Archival and Communication Systems), in which the images generated by modalities are stored in an image storage system or image archival system. Image viewing and image processing stations, known as workstations, are connected with one another via an image communication network to retrieve patient and image data.

Large image data sets are transferred and visualized in such medical system architectures, but often only a comparatively small transfer bandwidth is available.

The image data can be individual images, image series or volume datasets. Individual images that presently can be only transferred slowly are, for example, mammography images. An image series or multi-component images include, among other things, a set of individual images, known as image components, or simply components that have references to one another. Furthermore, in addition to the images, a multi-component image can include non-image information, for example ECG signals. The multi-component images can be, for example, CT slices the position of which can be established along the z-axis (the direction of the spiral track). Naturally, multi-component images can be generated not only with CT, but also with other modalities (for example by magnetic resonance techniques). Even volumes, as are acquired in 3D rotation angiography, can be considered as multi component images, as can image sequences that result from heart examinations. In the first case, the data exist in a common spatial coordinate system. In the second case, there are two spatial axes and one time axis that are common to all individual components.

To control interactive transfer of compressed multi-component data, parameters can be used that are freely adjustable within specific intervals. For example, compressed image data can be transferred with which, after receipt and decompression, an image sub-region (ROI) results with a selected resolution with required image quality. During the data transmission, however, an image display is already possible by which, for example, an image can be initially displayed at a lower resolution level with lower quality. As soon as more data are present, it then changes over to higher resolutions with better quality. This visualization procedure is designated as a progressive image representation.

Current image data compression methods such as JPEG-2000 or Motion JPEG-2000 are able to represent compressed individual image data and components of color images in a packet-based manner. Color images are, for example, spectral multi-component images in which all components are normally represented together as a color image. By targeted transfer of packets. JPEG-2000 offers the possibility to control the resolution, the section and the image quality of individual (color) images. The standardized JPEG-2000 (part 1) already offers important specifications for transfer of compressed image data and their progressive, multiple-resolution display. Packets can be generated with JPEG-2000 during the image data compression, with the compressed image data contents being described by the four parameters of image resolution (A), quality (Q), component index (K) and position in the image (ROI). JPEG-2000 also is able to write these data in a form known as a "codestream" that allows access to individual packets, however, part 1 only provides multi-component transformations in color images. This part of the standard therefore offers no possibility to generate individual components of a (medical) multi-component image with variable slice thickness. If it is desired to employ JPEG-2000, however, components could be generated using part 3 (Motion JPEG-2000), with variable slice thickness, by three gray components being considered as color components of an individual image and, for example, a reversible code transformation (RCT) being implemented. A "mean component" and two difference components are thereby obtained. The JPEG standard is described, for example, by Skodras et al. in "The JPEG 2000 Still Image Compression Standard", IEEE Signal Processing Magazine, pages 36 through 58, September 2001.

In additional to part 1, JPEG-2000 also provides, among other things, as part 10 (JP3D), the standardization process of which still is not completed. At present work is underway for finalizing this part of the JPEG-2000 standard and to create a reference implementation (known as a VM). A substantial difference of JP3D from the conventional JPEG-2000 approach may be that, in JP3D, a 3-D wavelet transformation will be provided to separate a volume that can ensue recursively along all three spatial directions. After the calculation of the wavelet transformation, the coefficients will be split into so-called "code blocks" (or "code cubes") and coded.

Designs also are available for the interactive transmission of image data that have been compressed with JPEG-2000. An interactive transfer of data packets of an image is already possible with the JPIP (JPEG-2000 Internet Protocol) discussed in this context.

The previous variants of JPIP, however, exhibit shortcomings. JPIP only makes available an incomplete set of metadate. Thus, the client is not able to determine, for example, the status of a specific received packet, since the "Unique Data Bin Identifier" used in JPIP provides no such information. With JPIP, this can possibly result in individual components of a large multi-component image being displayed with a different quality from the rest. This problem ensues particularly given large slice image data sets and slow data rates, for which a comparably long time can be required until consistent data for all slice images have been received. The calculation and rendering of large multi-component images also occupies a not-inconsiderable time. Therefore it is attempted to show images only at chosen points in time, in order to avoid visualization difficulties.

From the article by the company Merge Technologies Inc., "Image Channel™ White Paper" of 22 Apr. '02, a transfer system is known with which images, for example of a study, can be transferred from a server to a client with a specified resolution with progressive quality, as long as the images exist in JPEG-2000. Furthermore, the possibility exists to select ROIs using a low-resolution complete image. In this manner, corresponding data can be requested compressed that can then (after receipt and decompression) be shown in the highest resolution. Merge, as a producer of PACS software, assumes that the images are present in the DICOM format, however, only JPEG-2000 individual images exist in DICOM at present. Multi-component images with a number of individual slices that exist in the JPEG-2000 format are currently still not DICOM-compatible.

SUMMARY OF THE INVENTION

An object of the present invention is to provide a medical system architecture of the type initially described, as well as a corresponding method, wherein all acquired packets of the image data can be stored separately, and thus can be individually further processed later, with control signals being provided for the visualization.

This object is inventively achieved in a medical system architecture of the type initially described having a device that compresses and organizes the image data and stores them in packets with specific parameters such that access to individual packets is possible, and a device that decompresses the packetized image data packet-by-packet, based on a request by a user workstation, so that multi-component images such as image series or volumes are generated with progressive parameters.

The parameters can specify the resolution levels, the quality levels, the region of interest (ROI), the slice thickness and/or the component index, based on which multi-component images are generated with progressive resolution, progressive quality levels, consistent ROI functionality and/or variable slice thickness.

It has proven to be advantageous to communicate recommendations to the client that could help the client initiate directed actions when additional information and requirements are transmitted from the device to the user workstation (client). The image data thereby can be rendered (decompressed and displayed), or received data can be buffered in a consistent state.

In accordance with the invention the total data quantity to be transmitted can be transferred before processing to the user workstation with the current parameter settings, and/or the entire image file quantity can be transmitted in a compressed state to the user workstation before processing.

A representation of progress bars at the client allows control of which packets were already sent with which parameters when the device is fashioned such that the information are transmitted to the user workstation before processing.

An individual message can be transmitted to the user workstation after completion of the transfer of a consistent data set.

The message can be a render request or a storage recommendation.

Security aspects can also be considered when user rights ate associated with a user of a user workstation, based on which the device limits the image access with regard to specific parameters.

The object is inventively achieved in a method including via the steps of generating raw data of medical multi-component images with an imaging modality, generating compressed data from the raw data, organizing and storing the compressed image data in packets, such that access to individual packets is possible, transferring the compressed image data from metadata and from action recommendations, decompressing the compressed image data into multi-component images with progressive reproduction parameters.

Progress bars can be shown when queries ensue about image data with specific parameter values.

A limitation of the access of the different users to the image data can be achieved when a check of user rights ensues with regard to the parameters.

A transfer of supplementary information and requirements to the user workstation can inventively ensue.

The progressive reproduction parameters can be progressive resolution, progressive quality levels, consistent ROI functionality and/or variable slice thickness.

DESCRIPTION OF THE DRAWINGS

FIG. 4 illustrates a second example for a dialog between server and client in the system of FIG. 1.

DESCRIPTION OF THE PREFERRED EMBODIMENTS

Figure 1:
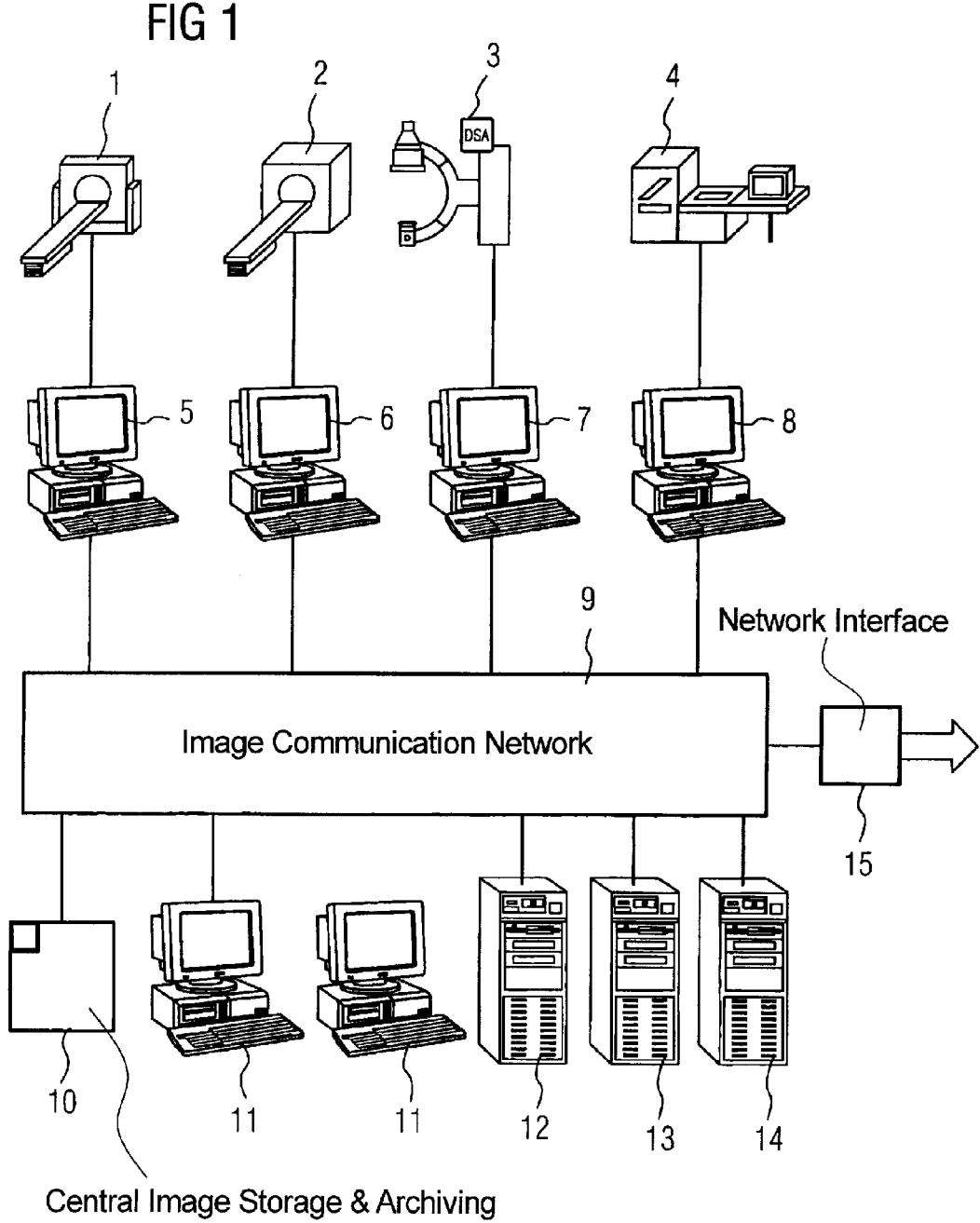
FIG. 1 schematically illustrates a system architecture in accordance with the invention in the example of a radiology department.

In FIG. 1, the system architecture of a hospital network in the example of an arrangement suitable for use in radiology. The modalities 1 through 4 (that, for example, can be image-generating systems such as a CT unit 1 for computed tomography, a MR unit 2 for magnetic resonance, a DSA unit 3 for digital subtraction angiography, and an x-ray unit 4 for digital radiography) serve to acquire medical images. Connected to these modalities 1 through 4 are operator consoles 5 through 8 of the modalities, serving as computer workstations, with which the acquired medical images can be processed and locally stored. Patient data belonging to the images can also be entered.

The operator consoles 5 through 8 are connected with a communication network 9 serving as a LAN/WAN backbone for distribution of the generated images and communication. Thus, for example, the images generated in the modalities 1 through 4 and the images further processed in the operator consoles 5 through 8 are stored in a central image storage and image archiving system 10 or are forwarded to other workstations.

Further viewing workstations, represented by a workstation 11, are connected to the communication network 9, for use as diagnostic consoles or computer workstations, that having local image storage. Such a viewing workstation 11 is, for example, a very fast minicomputer based on one or more fast processors. The acquired images stored in the image archiving system 10 can be subsequently retrieved to the viewing workstation 11 for making a diagnosis and are stored in the local image storage of the workstation 11, from which they are directly available to the diagnostician working at the viewing workstation 11.

Furthermore, a server 12 (for example patient data server (PDS), file server, program server and/or EPR server) is connected to the communication network 9. In addition to this common server or servers 12, a data server 13 and an image server 14 are connected to the communication network 9.

The image and data exchange via the communication network 9 ensues according to the DICOM standard, an industry standard for transmission of images and further medical information between computers with which digital communication is possible between diagnosis and therapy devices of different manufacturers. A network interface 15 can be connected to the communication network 9 via which the internal communication network 9 is connected with a global data network, for example the World Wide Web, such that the standardized data can be exchanged worldwide with different networks. Thus, for example, users in medical practices can also access the images.

Figure 2:
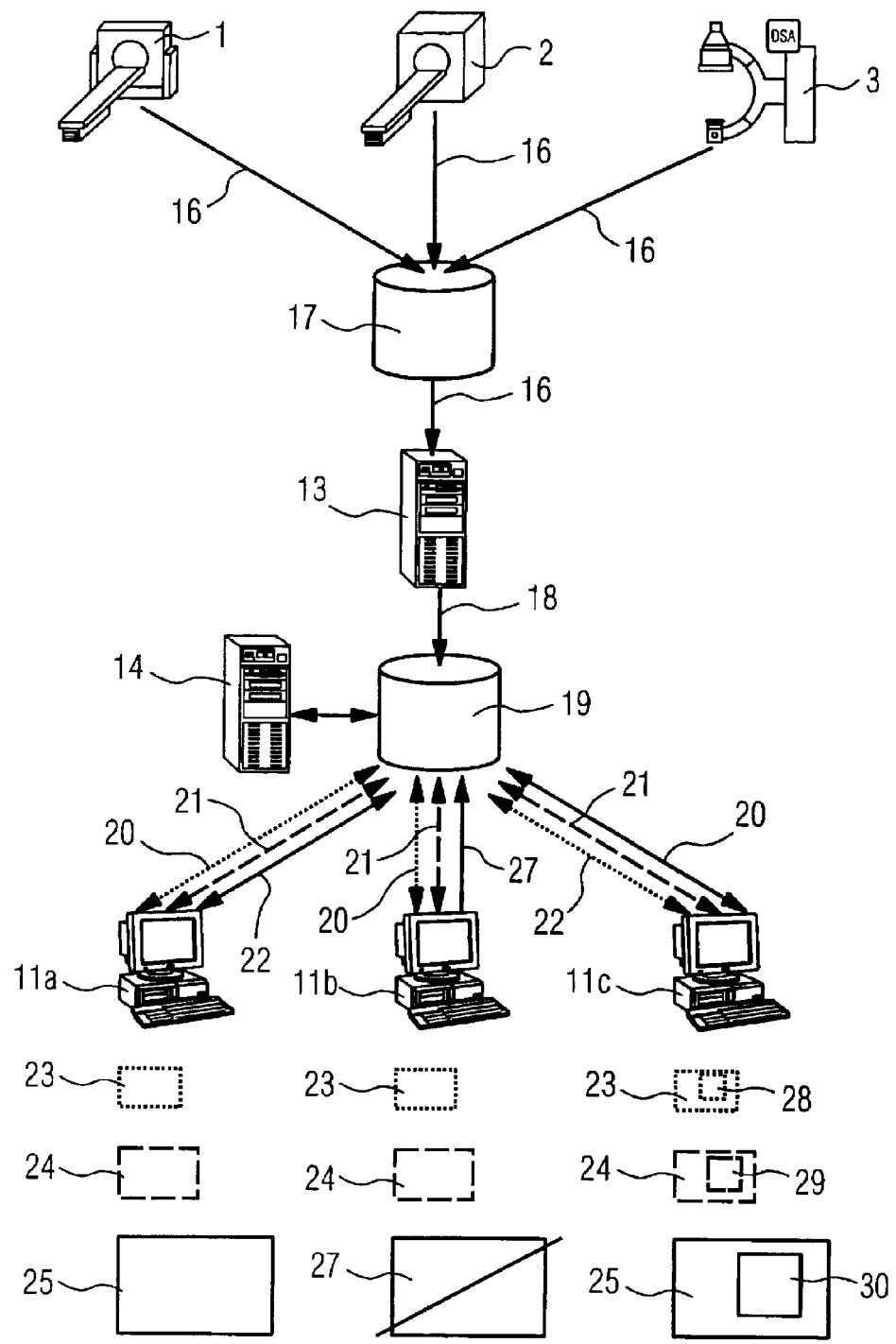
FIG. 2 illustrates system archiving and exemplary communication with three clients in the system of FIG. 1.

Schematically shown in FIG. 2 is the data flow from the imaging modalities 1 through 3 to users 11a through 11c at the workstations 11. Computers in medical practices also can be used in place of the workstations 11.

The situation is illustrated of the user 11a requesting a complete image, and receiving this complete image. The user 11b likewise requests the entire image, but the highest resolution is not delivered due to access rights. The user 11c requests only a partial section (ROI) from an image.

The raw data 16 are read in and stored from the imaging modalities 1 through 3 to a databank 17, as indicated by arrows. The raw data 16 stored in the databank 17 are converted by means of the data server 13 into compressed and packetized image data 18, for example JPEG-2000 code streams, which are stored in a second databank 19. The image server 14 is connected to this databank 19.

From this second databank 19, the user can retrieve the data packets via the workstation 11, with different hierarchies and access rights being associated with each user. Thus, for example, the user 11a can retrieve images with low, medium or high resolution from the databank 19, as indicated by the various dashed arrows 20 through 22 and the corresponding rectangles symbolizing the images 23 through 25. The user 11b can both retrieve and save the images 23 and 24 with low and medium resolution, however the user 11b is refused access to images 27 with the highest resolution, as symbolized by the arrow 27 and the lined-through rectangle. The arrow 27 also indicates the user 11b can store images with high resolution.

The same access rights are associated with the user 11c as with the user 11a, and additionally access is allowed to the regions of interest (ROIs) 28 through 30 in the images 23 through 25 with different resolutions. This is symbolized by the double arrows 20 through 22 and the correspondingly marked images 23 through 25 with the ROIs 28 through 30.

The data packets are supplied from the databank 19 to the users 11a through 11c based on the access rights and parameters specified by the respective users 11a through 11c that are explained below in detail, with the users 11a through 11c (client) or the image server 14 undertaking a selection of the data packets based on the parameters. A decompression of the data packets then ensues at the user 11a through 11c and, at a signal from the image server 14, a visualization of the previously transmitted image data ensues such that the image assembles.

Figure 3:
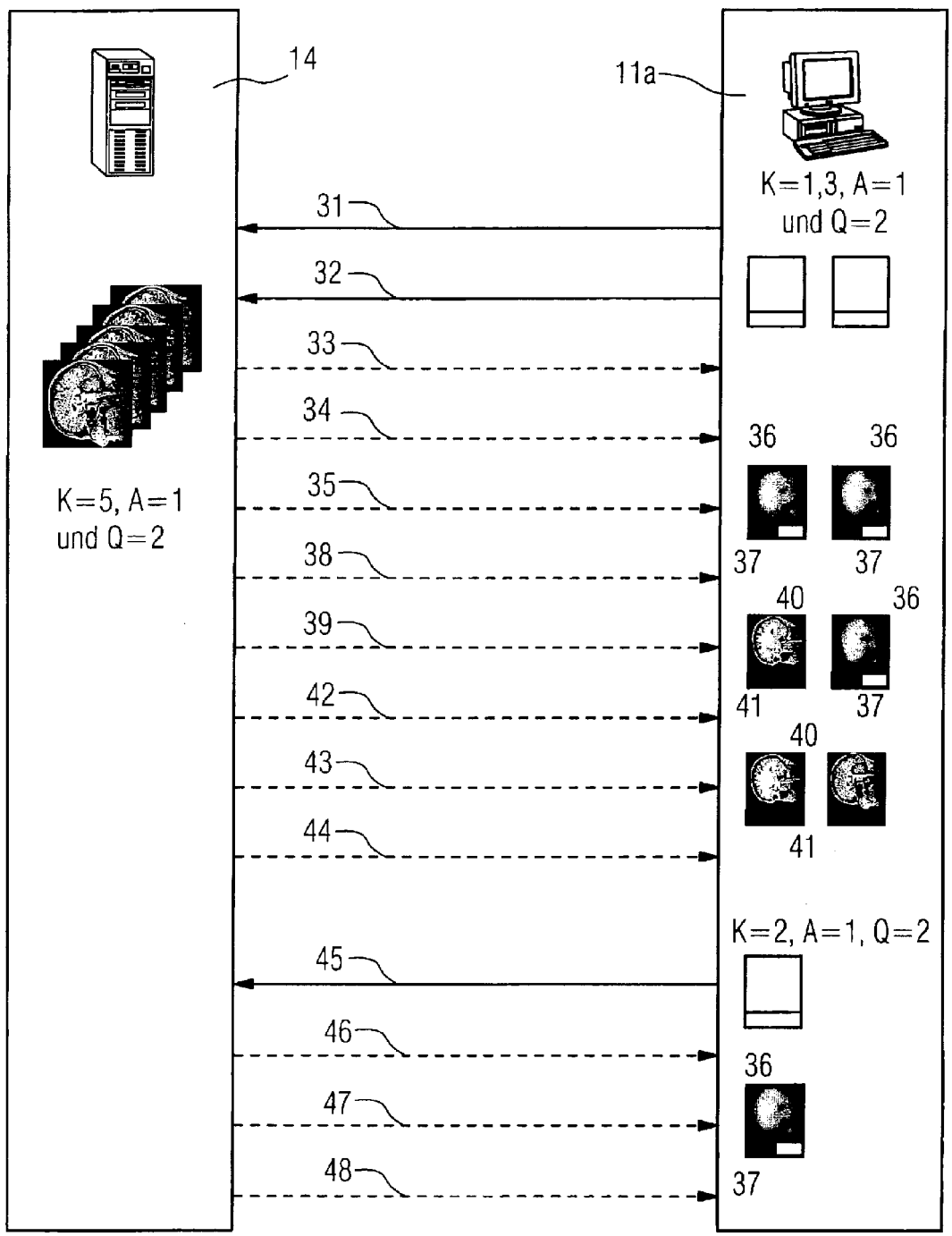
FIG. 3 illustrates a first example for a dialog between server and client in the system of FIG. 1.

In FIG. 3, the dialog between the image server 14 and the user 11a, a server-client communication, is shown for two different requests of the client to the server.

The illustrated monitor images on the right side of the user 11a are the result of individual, progressive rendering events at different points in time at the client (user 11a). Likewise, progress bars associated with the monitor images are to be seen on the client side. They show an exemplary graphical representation for the transmitted quality levels with which the individual components are shown (rendered) at the client.

As an example, image data of five components (K=5) are contained in the databank 19 that can be viewed with one resolution level (A=1) and two quality levels (Q=2). These image data can belong, for example, to five different slices of a CT examination.

First, the user 11a logs onto the image server 14 and transmits the authentication 31 with user name and password. The user 11a then sends a request 32 with which he requests, from the image data contained in the databank 19, the components one and three (K=1, 3) with a quality level two and the resolution level one.

Now the image server 14 transmits the data 33 for the first component (K=1, Q=1, A=1) to the user 11a in a first, low-quality level. The data 34 for the second component (K=3, Q=1, A=1) are subsequently transmitted with the first quality level. Now the image server 14 sends a rendering recommendation 35 for the components one and three, such that the user 11a can henceforth begin with the visualization of the date as this is to be seen on the monitor images 36 of lower quality level with the associated process or progress bars 37. Since the images have first been transmitted with a low quality, but also with a low data quantity, the monitor images 36 are still indistinct. The remaining data 38 for the component one are subsequently transmitted with a quality level two, based upon which the render recommendation 39 is subsequently transmitted from the server for this first component. A monitor image 40 with high quality is now compiled, and the progress bar 41 signals that the monitor image 40 is completely loaded for the component one. The monitor image 36 (situated next to it) for the component three, however, shows in the progress bar 37 that here only half of the data has been transmitted.

The data 42 for the component three are subsequently transmitted with high quality, and the render recommendation 43 is given. The second monitor image 40 also compiles the image with full quality, and the progress bar 41 shows that the compilation is complete. Finally, the image server 14 sends an information signal 44 to end the data transmission.

In a further step 45, the user 11a again requests the component two with a quality level one (K=2, Q=1, A=1). The data 46 for this component are transmitted from the image server 14 to the user 11a; the render recommendation 47 and the information 48 are subsequently transmitted via the end of the transmission.

A further dialog between the image server 14 and the user 11b is schematically shown in FIG. 4. In this communication, the client requests a resolution that is not allowed to him by the server, based on the defined user rights.

The progress bars 57, 58, 63 and 68 on the right side of the user 11b graphically represent the received data quantity relative to the total amount of image data. The progress bars 56, 62 and 67 associated with the monitor images show quality or resolution levels.

As an example, image data contained in the databank 19 with one component (K=1), three resolution levels (A=3) and two quality levels (Q=2) are considered.

First, the user 11b logs onto the image server 14 with his authentication 49 with user name and password. The user 11b then sends a request 50 with which he requests from the image data contained in the databank 19 the component (K=1) with a quality level two (Q=2) and the resolution level three (A=3).

Since, as already explained in FIG. 2, the user 11b has no access rights to the highest resolution level three, the image server 14 generates an error message 51 which it communicates to the user 11b that the resolution level three is not allowed.

The user 11b thereupon sends a new request 52 to the image server 14 with which he requests, from the image data contained in the databank 19, the component (K=1) with a quality level two (Q=2) and the (for the user 11b) maximum possible resolution level two (A=2).

The image server 14 now transmits to the user 11b the data 53 for the component (K=1, Q=1, A=1) at a first quality level and a first resolution level. The image server subsequently sends a render recommendation 54 for the component one, such that the client computer of the user 11b can henceforth begin the visualization of the data, as this is to be seen on the monitor image 55 of lesser quality level and low resolution with the associated progress bar 56. The progress bar 56 thereby shows the progress of the process of the data transmission with regard to the data quantity requested. A further provided progress bar 57 shows the progress of the process of the data transmission with regard to the total data quantity, such that the user 11b can recognize how much data (and therewith how much time) he would need if he were to retrieve all stored data. The progress bar 57 is empty up to the first data transmission 53. The progress bar 58 accordingly displays that a first small partial amount has been transmitted.

The data 59 (K=1, Q=2, A=1) are subsequently transmitted with a second quality level. The image server 14 now sends a render recommendation 60 for the component one, such that the monitor image 61 is to be seen with high quality level and low resolution with the associated progress bars 62 and 63.

The remaining data 64 are subsequently transmitted for the component one with a quality level two and medium resolution, whereupon the render recommendation 65 is subsequently transmitted from the image server 14. A monitor image 66 with high quality and medium resolution level is now assembled, and the progress bar 67 signals that the monitor image 66 for the component one is fully loaded, however, the progress bar 68 situated adjacent to it shows that only two-thirds of the total available data quantity has been transmitted.

To conclude, the image server 14 sends an information signal 69 at the end of a data transmission.

To send or load large image data sets of, for example, multi-component images via the communication network 9, the image data are first stored compressed form and then are transmitted compressed. It is important for the invention that the compressed data are organized such that they can be decompressed and displayed during the transmission of the complete data, directly after receipt of individual data packets, even when not all compressed data are present at the receiver.

Each ("grey") individual component can be of interest in these medical multi-component images. Therefore, JPEG-2000 will be extended such that, with the packets created then, both individual slice images and the entire data set can be progressively retrieved. In the first case, individual slices can be displayed in succession, for example progressively at different resolution levels and/or with variable quality. It is also possible to retrieve packets such that all components of a multi-component image are always present with uniform properties. Thus, a multi-component image at a specific resolution level can first be displayed in a uniform lower quality after the received has been decompressed. In the next step, further packets can then be requested with which all individual components are commonly brought to the next quality level. Such a procedure lends itself, for example, to a "movie mode" ("cine mode") in which the individual components are cycled slice by slice. Finally, the resolution level of all components can be uniformly increased by further data transfer. Given suitable data compression and organization of multi-component images, packet sequences can be transmitted such that both individual slice images and multi-component images can be progressively displayed.

In particular, a packet-oriented organization of the compressed image data, in which individual packets are associated with defined resolution and quality levels, allows individual images to represent components of an image series or volumes, or, respectively, ROIs thereof, for example with increasing spatial resolution and quality. In this context, image quality is understood as an error measurement that specifies the deviation between original image and displayed image after receipt of a part of the existing data. The error is low given a high image quality, and the greater the limitations in the image quality that are accepted, the greater the deviation from the original image, however, the more significantly the data to be transmitted is reduced.

Multi-component images can be visualized in different manners, for example as individual slices, by means of MPR (multiplanar reformations), MIP (maximum intensity projection), or using VR (volume rendering). A progressive procedure is also possible here, insofar as the data have been correspondingly generated and formatted/organized in the compression.

Moreover, the invention assumes a client-server system architecture that is based on what are known as sessions. The data transmission and image representation are thereby initiated by the client or user, whereupon the client receives, for example, an assigned identification number (ID) from the server. The same ID is then used for all further interactive client requests. The server can then hold in local storage a data model of the client, with which it can optimize the data transmission and representation. In order to achieve a desired image representation, however, the user can always change the settings of the transmission parameters independent of the server, whereby a real two-way communication results. The server is additionally authorized to change parameters that are specified by the client in the event that these are not consistent with the image.

The client also keeps the packets received from the server with the compressed image data separate in this form in the storage. Together with the existing image information, this offers the client the possibility to possibly later store only a segment of the transmitted data quantity, or to reuse it for further requests.

Given suitable user direction, the invention allows transmission decompression and display only of such specific data in compressed format that a user considers relevant. This can be a complete image at low spatial resolution or an image segment of the complete image in highest spatial resolution, in each case, the representation of the image data can ensue progressively, meaning that the image representation changes and improves with the amount of received data.

Access to individual packets is possible by the inventive application of data compression to medical multi-component images such as, for example, CT images or MR slice images, whereby the compressed image data is organized and stored in packets. Dependent on how selected packets are transmitted, after their decompression multi-component images (for example image series or volumes) can be generated with progressive resolution, progressive quality levels, consistent ROI functionality and/or variable slice thickness. The idea of a progressive slice thickness thereby serves to obtain voxels at each resolution level that exhibit in all dimensions the optimally identical dimensions (isotropic voxels). Direct access to individual components is naturally also possible.

In the session-based client-server system architecture for packet-based, interactive request and transmission of compressed medical image data such as images, image series and volumes, client requests are communicated to a server via specific parameter values. This system is in particular characterized by, during the data transmission, the server communicating to the client additional information and requests that have not as of yet been considered in JPIP. The preparation of supplementary information and of requests from the server to a client serves for user direction and to specifically instigate specific actions at the client such as, for example, the rendering of an image series at a specific resolution with a specific quality. In particular, the following information is important:
a. total data quantity of the image or, respectively, the expected data quantity of the image section given the current parameter settings,
b. ongoing disclosure to the client about which packets have already been sent with which parameters, such as resolution levels, quality levels, ROI, slice thickness and/or component index, in order to control the representation of progress bars at the client, and/or
c. individual messages transmitted from the server to the client, for example render recommendations or storage recommendations, as soon as a consistent data set has already been completely transmitted.

The image accesses can be limited via the inventive, server-side security storage of the image data using predetermined user rights. Dependent on the user rights, compressed image data may only be requested with specific parameters. For example, the image resolution, the image quality and the image section can be restricted for users with lower level rights. Moreover, given image series the access to certain individual images can be barred. Such user rights, for example, can be developed on the server via a system that identifies users by means of login and password.

If a suitable compression method (for example a wavelet compression method) is applied not only to individual components of a multi-component image, but rather in this context successive components are also sent separated and combined, then what are known as "mean components" and "difference components" are obtained. The mean components can be understood as a new multi-component image in which fewer components exist with correspondingly enlarged slice thickness. The advantage of a variable slice thickness is that an approximately isotropic voxel size can be achieved given the progressive transmission and visualization of multi-component images at each resolution level.

If the total data quantity of the image or the total data quantity of the expected data for a selected image section dependent on current specified parameters is known, then it can be established given monitoring of the already-received data quantity at the client how much data have already been transmitted relative to the respective total data quantity or what portion is still expected. The progress bars 37, 56 and 57, etc., that communicate to the user how the data transmission or the quality of the received images progresses, can thus be controlled. Given very slow transmission channels, this information allows a user, for example, to end the transmission of an entire image in highest resolution and alternatively request only a portion thereof.

The properties of the compressed multi-component image, the component number, resolution levels, number of quality levels and, as needed, also the slice thickness curve normally are known because they are communicated at the beginning of a data transmission. If one then has information about the already-received packets and the parameters associated therewith, this information can likewise be used for user direction. For example, a progress bar can newly display which quality level has previously been achieved, which has been requested, and which is the highest possible level. A similar representation can be achieved when, initially a few individual slices with large thickness are sent that then become ever thinner, and thus more detailed, given receipt of further data.

A communication from the image server 14 to the client 11 as soon as the transmission of all packets with a specific parameter is concluded can serve to initiate a specific event. Thus, for example, a visualization event can be triggered or received data can be buffered. It can thereby be assured at the client that, for example, all components of an image series or all voxels of a volume data set are present with uniform properties. If the communication proceeds differently and, for example, operates time-controlled, for example every 10 ms, then it is not improbable that components of an image series of voxels of a volume will differ with regard to their parameters at a specific point in time, for example, by exhibiting a different quality or resolution level. An agreement on the smallest common parameter of all components ensues either upon rendering or storage, or the data are processed with different properties.

The inventive client-server system is therefore able to make decisions based on user information and user rights a to who may request and see which data with which parameters. A server can thereby check whether a user is actually entitled to implement a request with the parameters desired by him. For example, the image server 14 could refuse to let a specific class of users see image data or sections thereof at high resolution levels or high qualities. Furthermore, it is possible in the case of image series to bar the access to certain individual components.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical system architecture for interactive transmission and progressive representation of compressed image data of multi-component images, comprising:

at least one imaging modality that acquires image data from a subject representing examination images each having a slice thickness within the subject from which said image data are obtained;

for each imaging modality, a computer workstation associated therewith that processes the image data acquired by the associated imaging modality;

a communication network in communication with said computer workstation that transfers said examination images, after processing in the computer workstation, to locations remote from said computer workstation;

a storage device in communication with said communication network that stores said examination images;

at least one further workstation in communication with said communication network that post-processes the examination images processed in said computer workstation;

a compression device in communication with said computer network that compresses and organizes the image data representing said examination images and stores the compressed data in packets, as packetized image data, with a parameter linked to the respective packets, said parameter defines permissible access to the respective packets, and specifies a slice thickness progression; and a decompression device in communication with said communication network that decompresses the packetized image data packet-by-packet dependent on a request from said further workstation and dependent on said parameter, to cause a multi-component image to be generated at said further workstation composed of a plurality of said examination images, with the respective examination images in said multi-component images having a selectively variable slice thickness, along said slice thickness progression, that is selected dependent on said parameter.

2. A medical system architecture as claimed in claim 1 wherein said compression device generates further parameters respectively linked with said packets in addition to said parameter specifying slice thickness, selected from the group consisting of a parameter specifying an image resolution level, a parameter specifying an image quality level, a parameter specifying a region of interest, and a parameter specifying a component index, and wherein said decompression device employs said parameters to generate said multi-component images with at least one of a progressive image resolution, progressive image quality levels, and consistent region of interest presentation, respectively.

3. A medical system architecture as claimed in claim 1 wherein said compression device generates supplementary information and requests and transmits said supplementary information and requests to said further workstation together with the compression packetized image data.

4. A medical system architecture as claimed in claim 1 wherein said compression device transmits a total quantity of data in compressed state, with said parameters, to said further workstation.

5. A medical system architecture as claimed in claim 1 wherein said compression device transmits an entire file for an image in compressed state to said further workstation.

6. A medical system architecture as claimed in claim 1 wherein said compression device transmits information identifying packets that have already been sent and parameters that have already been transmitted in advance to said further workstation.

7. A medical system architecture as claimed in claim 1 wherein said compression device generates and communicates a message to said further workstation after conclusion of transferring a consistent set of said image data.

8. A medical system architecture as claimed in claim 7 wherein said compression device generates and transmits a render request as said message.

9. A medical system architecture as claimed in claim 7 wherein said compression device generates and transmits a storage recommendation as said message.

10. A medical system architecture as claimed in claim 1 wherein said further workstation has user rights associated therewith, and wherein said compression device transmits the compression packetized image data, or portions thereof, to said further workstation dependent on said user rights.

* * * * *